United States Patent
Wada (12)

(10) Patent No.: US 10,258,511 B2
(45) Date of Patent: Apr. 16, 2019

(54) FOLDING DEVICE AND FOLDING METHOD USING SAME

(71) Applicant: ZUIKO CORPORATION, Osaka (JP)

(72) Inventor: Takao Wada, Osaka (JP)

(73) Assignee: Zuiko Corporation (JP)

( * ) Notice: Subject to any disclaimer, the term of this patent is extended or adjusted under 35 U.S.C. 154(b) by 472 days.

(21) Appl. No.: 15/030,393

(22) PCT Filed: Oct. 10, 2014

(86) PCT No.: PCT/JP2014/077169
§ 371 (c)(1),
(2) Date: Apr. 19, 2016

(87) PCT Pub. No.: WO2015/060142
PCT Pub. Date: Apr. 30, 2015

(65) Prior Publication Data
US 2016/0242968 A1    Aug. 25, 2016

(30) Foreign Application Priority Data

Oct. 25, 2013    (JP) .................................. 2013-222179

(51) Int. Cl.
*A61F 13/15* (2006.01)
*B65H 45/22* (2006.01)
(Continued)

(52) U.S. Cl.
CPC .. *A61F 13/15747* (2013.01); *A61F 13/15764* (2013.01); *B65H 5/021* (2013.01);
(Continued)

(58) Field of Classification Search
CPC .......... A61F 13/15593; A61F 13/15747; A61F 13/15764; B65H 2801/57; B65H 45/22; B65H 45/30; B65H 5/021
(Continued)

(56) References Cited

U.S. PATENT DOCUMENTS

| | | | | |
|---|---|---|---|---|
| 4,488,927 | A | * | 12/1984 | Hooper ............. A61F 13/15747 156/464 |
| 4,900,384 | A | * | 2/1990 | Sanders ............ A61F 13/15593 156/164 |

(Continued)

FOREIGN PATENT DOCUMENTS

| | | | |
|---|---|---|---|
| EP | 0 240 872 | 10/1987 | |
| EP | 0240872 A1 | * 10/1987 | ............. B65H 45/22 |

(Continued)

OTHER PUBLICATIONS

European Search Report dated Aug. 9, 2016.
International Search Report.

*Primary Examiner* — Hemant Desai
*Assistant Examiner* — Valentin Neacsu
(74) *Attorney, Agent, or Firm* — Gerald E. Hespos; Michael J. Porco; Matthew T. Hespos

(57) ABSTRACT

A folding device includes a folding mechanism configured to form a first folding line extending from one widthwise end of a sheet, a second folding line extending obliquely from the other widthwise end of the sheet toward an end of the first folding line and a third folding line configured to reverse one widthwise part of the sheet such that one widthwise part of the sheet folded along the second folding line overlaps with another part. The folding mechanism includes a second folding member having a second folding line forming portion configured to form the second folding line. The second folding member is so attached to a conveying mechanism that the second folding line forming portion is movable with respect to the formation positions of the first folding line and the third folding line.

8 Claims, 8 Drawing Sheets

(51) Int. Cl.
  *B65H 5/02* (2006.01)
  *B65H 45/30* (2006.01)
(52) U.S. Cl.
  CPC ............. *B65H 45/22* (2013.01); *B65H 45/30* (2013.01); *A61F 13/15593* (2013.01); *B65H 2801/57* (2013.01)
(58) Field of Classification Search
  USPC .................................. 493/440, 23, 405, 439
  See application file for complete search history.

(56) References Cited

U.S. PATENT DOCUMENTS

| | | | | |
|---|---|---|---|---|
| 4,905,451 | A * | 3/1990 | Jaconelli | B65B 11/045 493/440 |
| 5,152,738 | A * | 10/1992 | Zehender | B65H 45/22 493/439 |
| 5,190,606 | A * | 3/1993 | Merkatoris | A61F 13/15593 156/164 |
| 5,827,387 | A * | 10/1998 | Reynolds | A61F 13/15593 156/164 |
| 6,277,223 | B1 * | 8/2001 | Herrin | A61F 13/15804 156/163 |
| 7,785,309 | B2 * | 8/2010 | Van Gompel | A61F 13/4942 604/385.01 |
| 2003/0211923 | A1 * | 11/2003 | Harnish | B65H 23/02 493/23 |
| 2005/0026760 | A1 * | 2/2005 | Yamamoto | A61F 13/15747 493/81 |
| 2006/0151091 | A1 * | 7/2006 | Komatsu | A61F 13/15593 156/161 |
| 2009/0217624 | A1 * | 9/2009 | Forrest | B65B 11/006 53/399 |
| 2010/0050411 | A1 * | 3/2010 | Yamamoto | A61F 13/15747 29/428 |
| 2013/0059714 | A1 * | 3/2013 | Yamamoto | A61F 13/15747 493/405 |

FOREIGN PATENT DOCUMENTS

| | | |
|---|---|---|
| JP | 62-255359 | 11/1987 |
| JP | 6-083663 | 11/1994 |
| JP | 07-136208 | 5/1995 |
| JP | 2698791 | 9/1997 |
| JP | 2011-178533 | 9/2011 |
| WO | 03095349 A1 | 11/2003 |

* cited by examiner

FOLDING DEVICE AND FOLDING METHOD USING SAME

TECHNICAL FIELD

The present invention relates to a folding device for folding a sheet in a width direction while conveying the sheet in a longitudinal direction and a folding method using the same.

BACKGROUND ART

Conventionally, there has been known a device for folding a sheet in a width direction to overlap one widthwise part of the sheet with another part while conveying the sheet in its longitudinal direction (e.g. Publication of Japanese Patent No. 2698791).

FIGS. 9A and 9B are perspective views enlargedly showing an essential part of a device described in the Publication of Japanese Patent No. 2698791, wherein FIG. 9A shows a state where a sheet is being folded and FIG. 9B shows the state of FIG. 9A with the sheet omitted.

The device of Publication Japanese Patent No. 2698791 includes an upstream side plate 30 and a downstream side plate 31 and a sheet S2 is conveyed in its longitudinal direction while being held in contact with the both plates 30, 31 as indicated by an arrow of FIG. 9A.

The upstream side plate 30 has an edge part 30a for forming a first folding line B5 of the sheet S2 and an edge part 30b for forming a second folding line B6 of the sheet S2.

The first folding line B5 is a folding line extending in the width direction from one widthwise end S21 to a widthwise intermediate part of the sheet S2.

The second folding line B6 extends obliquely to a conveying direction from the other widthwise end S22 of the sheet S2 at a position upstream of the first folding line B5 toward an end of the first folding line B5.

The downstream side plate 31 has an edge part 31a for forming a third folding line B7 for reversing one widthwise part of the sheet S2 such that the one widthwise part of the sheet S2 folded along the second folding line B6 overlaps with another part.

The third folding line B7 extends obliquely to the conveying direction from the end of the first folding line B5 toward the other widthwise end S22 of the sheet S2 to be reversed.

In the device described in the Publication of Japanese Patent No. 2698791, the plates 30, 31 are fixed to each other. That is, the respective edge parts 30a, 30b and 31a for forming the first to third folding lines B5 to B7 are fixed to each other.

Thus, there is a problem that an area of the sheet S2 on the side of the other widthwise end S22 located between the second and third folding lines B6, B7 is not suitable for folding and. Therefore, the sheet S2 cannot be folded precisely in the case of changing a thickness of the sheet S2 or changing a tension applied to the sheet S2.

SUMMARY OF INVENTION

The present invention aims to provide a folding device capable of precisely folding a sheet even in the case of changing a thickness of the sheet or a tension applied to the sheet and a folding method using the same.

To solve the above problem, the present inventors arrived at an invention relating to a device capable of relatively adjusting the formation positions of a second folding line and a third folding line of a sheet.

However, since the third folding line specifies a sheet folding start point in cooperation with a first folding line, the folding of the sheet itself may become impossible if the formation positions of the first and third folding lines are relatively changed.

Accordingly, the present inventors arrived at an invention relating to the following device capable of adjusting the formation position of a second folding line with respect to those of first and third folding lines.

Specifically, the present invention provides a folding device for folding a sheet in a width direction such that one widthwise part of the sheet overlaps with another part while conveying the sheet in a longitudinal direction thereof, the folding device including a conveying mechanism configured to convey the sheet in the longitudinal direction, and a folding mechanism configured to form a first folding line, a second folding line and a third folding line of the sheet being conveyed by the conveying mechanism, the first folding line extending in the width direction from one widthwise end to a widthwise intermediate part of the sheet, the second folding line extending obliquely to the longitudinal direction from the other widthwise end of the sheet on a side upstream of the first folding line in a conveying direction toward an end of the first folding line and the third folding line being configured to reverse one widthwise part of the sheet such that one widthwise part of the sheet folded along the second folding line overlaps with another part on a side downstream of the first folding line in the conveying direction, wherein the folding mechanism includes a second folding member having a second folding line forming portion configured to form the second folding line of the sheet, and the second folding member is so attached to the conveying mechanism that the second folding line forming portion is movable with respect to the formation positions of the first and third folding lines of the sheet.

Further, the present invention provides a folding method for folding a sheet in a width direction such that one widthwise part of the sheet overlaps with another part using the above folding device, the folding method including a conveying step of conveying the sheet in a longitudinal direction thereof using the conveying mechanism, a folding line forming step of forming a first folding line, a second folding line and a third folding line of the sheet being conveyed by the conveying step using the folding mechanism, the first folding line extending in the width direction from one widthwise end to a widthwise intermediate part of the sheet, the second folding line extending obliquely to the longitudinal direction from the other widthwise end of the sheet on a side upstream of the first folding line in a conveying direction toward an end of the first folding line and the third folding line being configured to reverse one widthwise part of the sheet such that one widthwise part of the sheet folded along the second folding line overlaps with another part on a side downstream of the first folding line in the conveying direction, and an adjusting step of adjusting a folded state of the sheet by moving the second folding line forming portion of the second folding member with respect to the formation positions of the first and third folding lines prior to the folding line forming step.

According to the present invention, the sheet can be precisely folded even in the case of changing a thickness of the sheet or a tension applied to the sheet.

DESCRIPTION OF EMBODIMENT

Hereinafter, an embodiment of the present invention is described with reference to the accompanying drawings. Note that the following embodiment is a specific example of the present invention and not of the nature to limit the technical scope of the present invention.

First, a sheet folding operation performed by a folding device of the present invention is described with reference to FIG. 1.

The folding device according to the present invention is configured to fold a sheet S1 in a width direction such that one widthwise part of the sheet S1 overlaps with another part while conveying the sheet S1 in its longitudinal direction as indicated by an arrow Y1 (hereinafter, referred to as a conveying direction Y1).

Specifically, the sheet S1 is folded as follows in its conveyance process.

The sheet S1 is folded along a first folding line B1 extending in the width direction from one widthwise end S11 to a widthwise intermediate part thereof. In this way, the conveying direction Y1 is bent at a position corresponding to the first folding line B1.

Further, the sheet S1 is folded along a second folding line B2 extending obliquely to the conveying direction Y1 of the sheet S1 from the other widthwise end S12 of the sheet S1 on a side upstream of the first folding line B1 in the conveying direction Y1 toward an end of the first folding line B1.

One widthwise part of the sheet S1 folded along the second folding line B2 is so folded along a fourth folding line B4 as to be parallel to another widthwise part of the sheet S1 on a side downstream of the first folding line B1.

One widthwise part of the sheet S1 folded along the fourth folding line B4 is so reversed along a third folding line B3 as to overlap with another part. Note that the third folding line B3 extends obliquely to the conveying direction from the end of the first folding line B1 toward the other widthwise end S12 of the sheet S1 to be reversed.

As just described, the sheet S1 is so folded that the one widthwise part thereof overlaps with the other part by being folded along the first to fourth folding lines B1 to B4 in its conveyance process.

Figure 1:
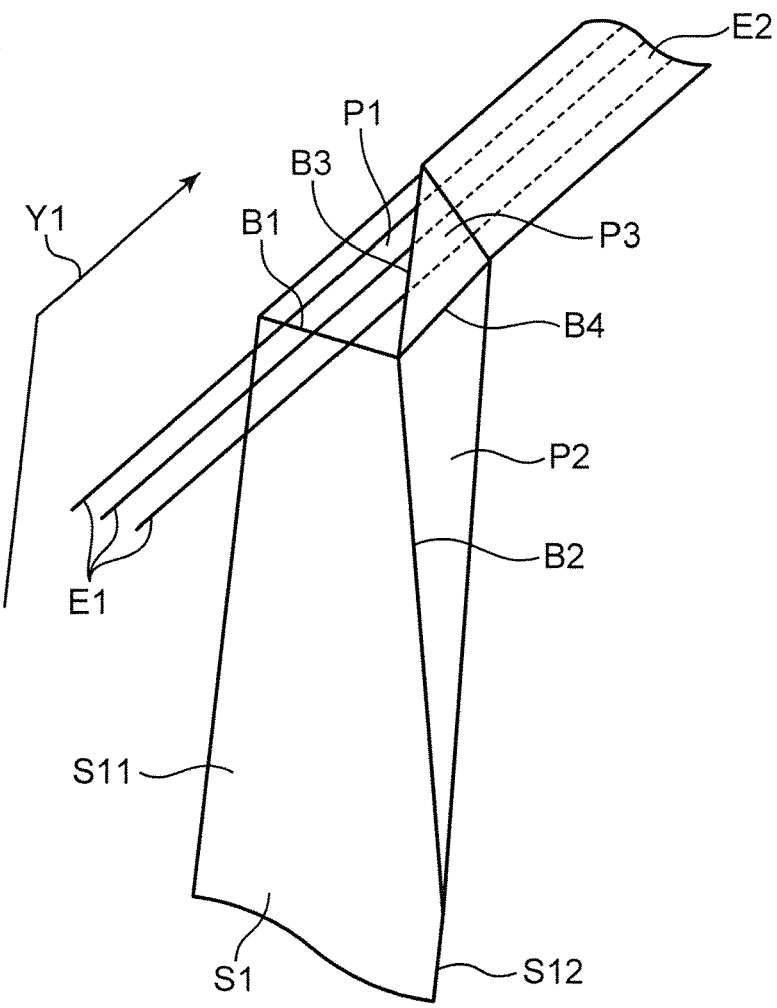
FIG. 1 is a process diagram showing a sheet folding operation performed by a folding device according to an embodiment of the present invention.

Further, in the folding device according to the embodiment of the present invention, a plurality of elastic members E1 (three elastic members E1 are shown in FIG. 1) are supplied in a stretched state to between the parts of the sheet S1 to be folded from an unillustrated supplying device.

Since an adhesive is supplied to the sheet S1 and/or the elastic members E1 on a side upstream of the folding device, a sheet-like elastic body E2 is produced by folding the sheet S1 to sandwich the elastic members E1 in the folding device.

Figure 2:
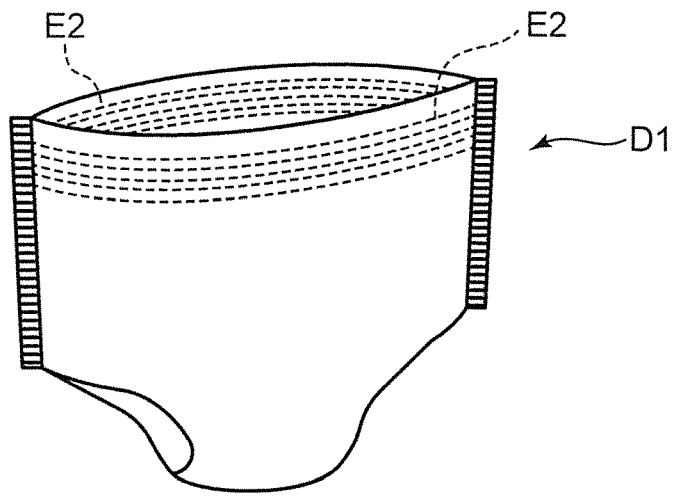
FIG. 2 is a schematic diagram showing a disposable diaper to which a sheet-like elastic body produced using the folding device according to the embodiment of the present invention is applied.

This sheet-like elastic body E2 can be utilized, for example, as an elastic member for waist of a disposable diaper D1 as shown in FIG. 2.

Hereinafter, a folding device 1 according to the embodiment of the present invention is described with reference to FIGS. 1 to 3.

The folding device 1 includes a conveying mechanism 2 for conveying the sheet S1 in a longitudinal direction along a conveyance path R1 bent at a part corresponding to the first folding line B1, a second folding mechanism 3 for forming the second folding line B2 of the sheet S1 being conveyed by the conveying mechanism 2, a third folding member 4 for forming the third and fourth folding lines B3, B4 of the sheet S1 being conveyed by the conveying mechanism 2 and a supporting portion 5 for supporting the conveying mechanism 2, the second folding mechanism 3 and the third folding member 4.

Note that, in the following description, a direction along a path downstream of the first folding line B1 in the conveyance path R1 of the sheet S1 is referred to as an X direction, a width direction of the sheet S1 as a Y direction and a direction orthogonal to an X-Y plane as a Z direction.

Figure 5:
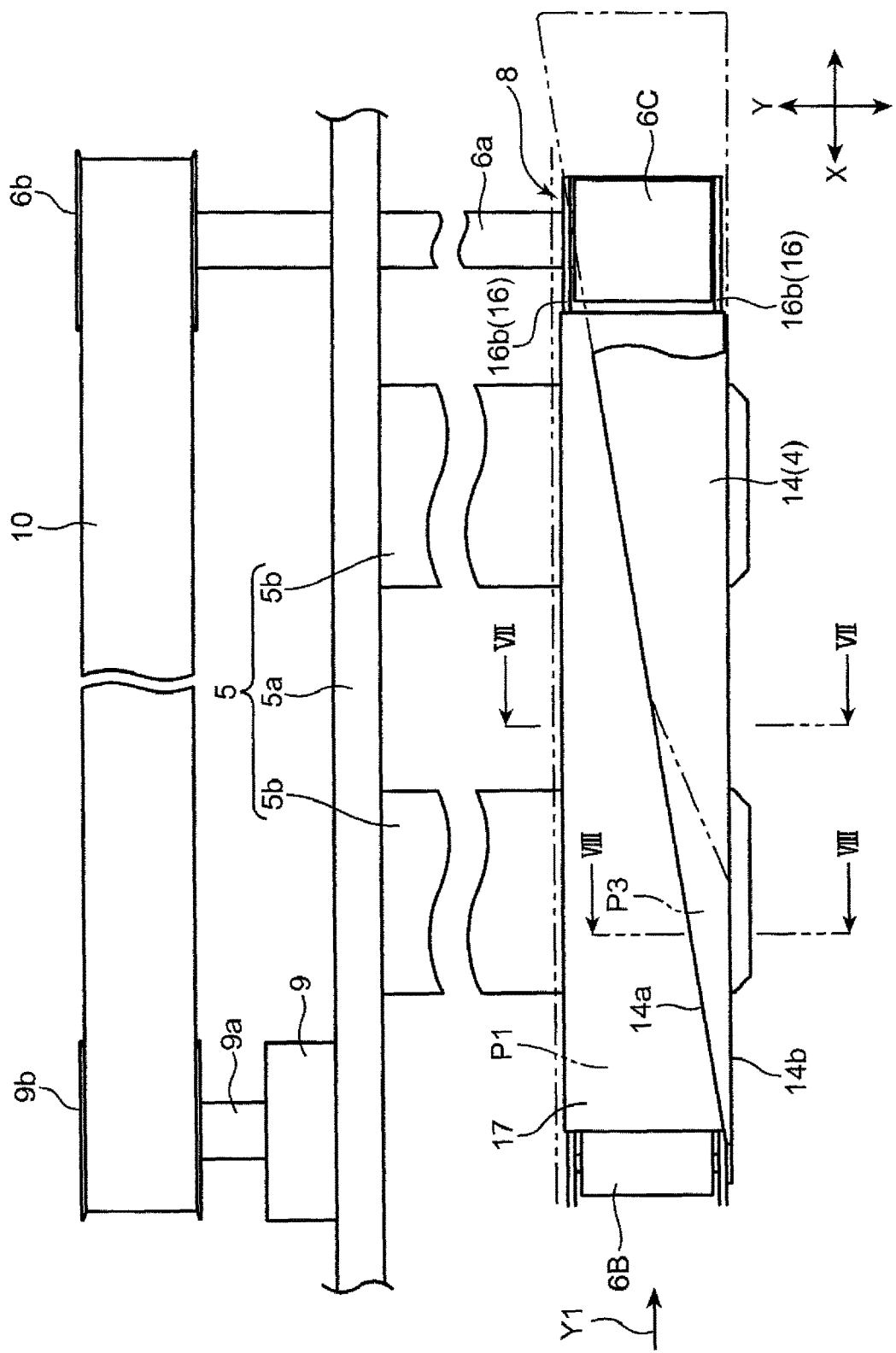
FIG. 5 is a view indicated by an arrow V of FIG. 3.

The conveying mechanism 2 includes a conveying belt 7, three pulleys 6A to 6C having the conveying belt 7 provided thereon along an annular path including the conveyance path R1, a pulley supporting portion 8 for supporting the pulleys 6A to 6C and a motor 9 (see FIG. 5) for transmitting power to the pulleys 6A to 6C via a drive belt 10 (see FIG. 5).

The conveying belt 7 is circulated in a direction to move to the pulley 6A again via the pulleys 6A, 6B and 6C in this order by driving the motor 9.

The pulleys 6B, 6C are arranged to hold the conveying belt 7 on the same X-Y plane. Further, the pulley 6A is provided at a position different from the pulleys 6B, 6C in the Z direction (lower position of FIG. 3).

That is, the pulley 6B is provided at a bent position of the conveyance path R1 to form the first folding line B1 of the sheet S1 held in contact with the pulley 6B via the conveying belt 7.

With reference to FIGS. 3 to 7, the pulley supporting portion 8 includes a pair of side plates 16 supporting the pulleys 6A to 6C from opposite sides in the Y direction. Belt supporting plates 17 are fixed respectively to the side plates 16 along the conveyance path R1 and support the inner side surface of the conveying belt 7. Additionally, bottom plates 18 are fixed respectively to the side plates 16 and face the belt supporting plates 17. Note that the conveying belt 7 is not shown in FIGS. 4 and 5.

Figure 3:
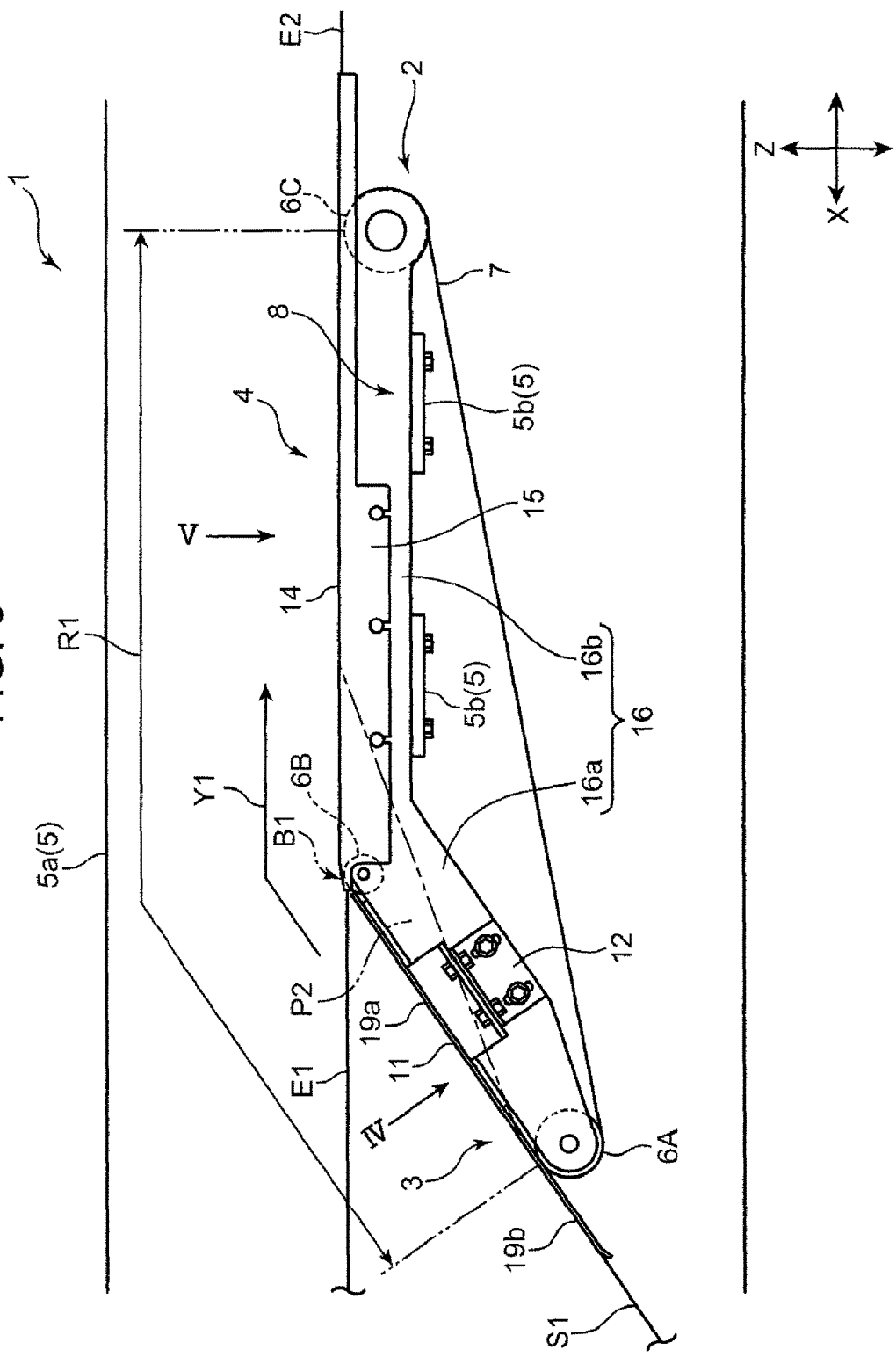
FIG. 3 is a schematic side view showing an overall configuration of the folding device according to the embodiment of the present invention.

As shown in FIG. 3, the side plate 16 includes an upstream portion 16a arranged along a part of the conveyance path R1 specified by the pulleys 6A and 6B and a downstream portion 16b arranged along a part of the conveyance path R1 along a part specified by the pulleys 6B and 6C.

One belt supporting plate 17 is provided on the upstream portions 16a of the side plates 16 and one belt supporting plate 17 is provided on the downstream portions 16b of the side plates 16, as shown in FIGS. 4 to 7. The belt supporting plates 17 are fixed to end surfaces of the side plates 16 with the pulleys 6A to 6C exposed for the conveying belt 7.

Similarly, one bottom plate 18 is provided on the upstream portions 16a of the side plates 16 and one bottom plate 18 is provided on the downstream portions 16b of both side plates 16. The bottom plates 18 are fixed respectively end parts of the side plates 16 opposite to the belt supporting plates 17.

Figure 7:
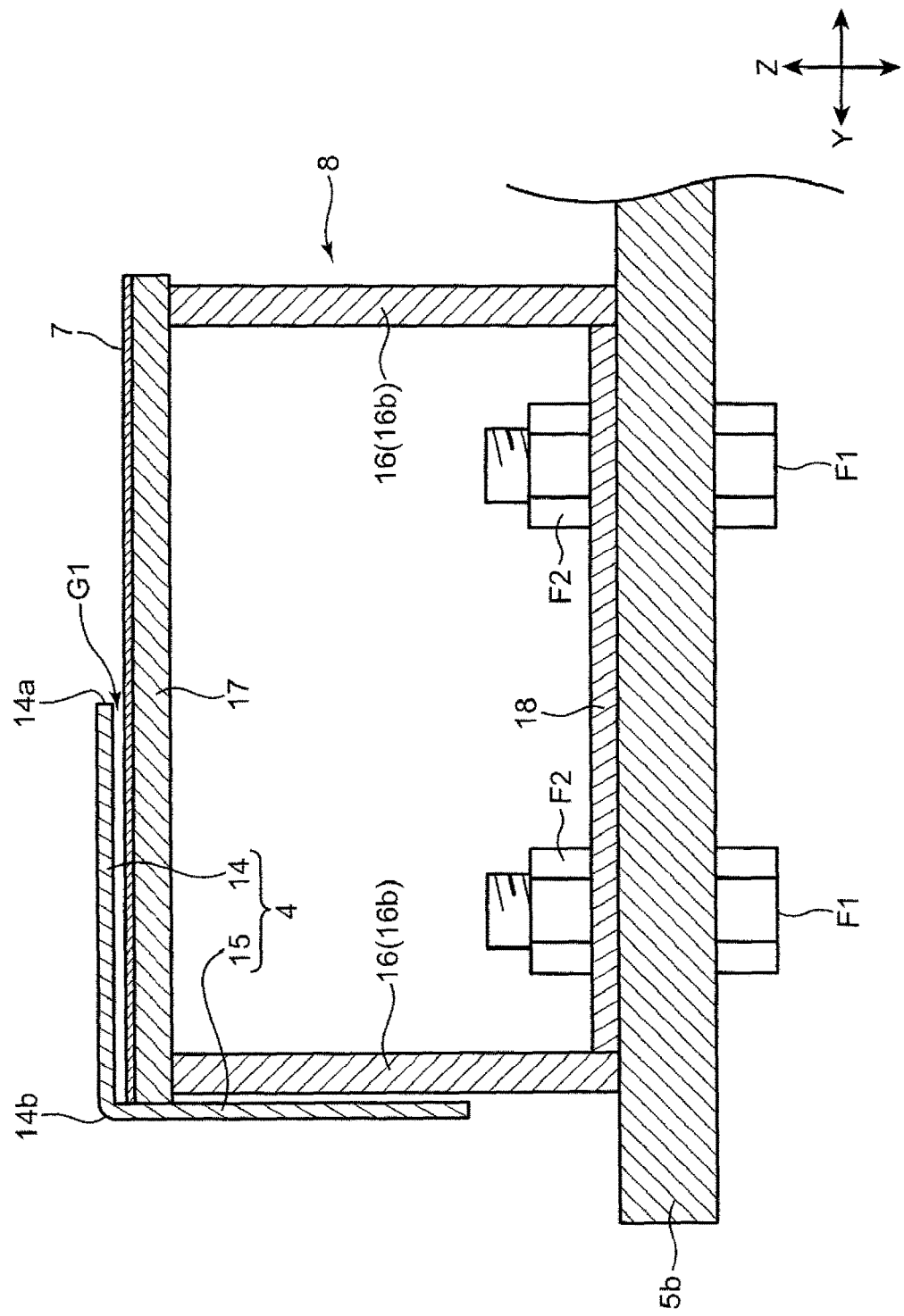
FIG. 7 is a sectional view along line VII-VII of FIG. 5.

Here, as shown in FIGS. 5 and 7, the pulley supporting portion 8 is supported on the supporting portion 5 on the bottom plate 18 provided on the downstream portions 16b.

The supporting portion 5 includes a main frame 5a provided on one side of the pulley supporting portion 8 in the Y direction and a pair of supporting arms 5b projecting toward the pulley supporting portion 8 from the main frame 5a.

The pulley supporting portion 8 is fixed to the both supporting arms 5b by bolts F1 penetrating through the bottom plates 18 and the supporting arms 5b and nuts F2 threadably engaged with the bolts F1 while being placed on the both supporting arms 5b.

With reference to FIG. 5, the motor 9 is fixed to the main frame 5a and supplies power to the pulley 6C via the drive belt 10.

Specifically, a pulley 9b is provided on a rotary shaft 9a of the motor 9 and a pulley 6b is provided on a rotary shaft 6a of the pulley 6C, the drive belt 10 being provided on the pulley 6b and the pulley 9b.

The second folding mechanism 3 is described below with reference to FIGS. 1, 3, 4 and 6.

The second folding mechanism 3 is so attached to the upstream portion 16a of the side plate 16 distant from the main frame 5a of the pulley supporting portion 8 as to face in a direction away from the main frame 5a.

The second folding mechanism 3 includes a second folding member 11 for bending the sheet S1 along the second folding line B2 and a bracket 12 for attaching the second folding member 11 to the pulley supporting portion 8.

The second folding member 11 includes a second folding portion 19 having a trapezoidal planar shape and an attaching portion 20 for attaching the second folding portion 19 to the bracket 12.

The second folding portion 19 includes a supporting surface 19b for supporting one widthwise part of the sheet S1 being conveyed by the conveying mechanism 2 and a second folding line forming portion 19a for forming the second folding line B2 of the sheet S1. The second folding line forming portion 19a is an edge part of the second folding portion 19 inclined in a direction to approach the conveying mechanism 2 in the Y direction toward the conveying direction Y1.

The attaching portion 20 is configured to attach the second folding portion 19 to the bracket 12 such that the supporting surface 19b of the second folding portion 19 is arranged side by side with the conveying belt 7 in the Y direction.

Further, the attaching portion 20 is configured to attach the second folding portion 19 to the bracket 12 such that the second folding portion 19 is movable relative to the conveying mechanism 2 in a moving direction Y2 (see FIG. 4) along the conveying direction Y1. Specifically, the attaching portion 20 includes a part extending along the side plate 16 from an end part of the second folding portion 19 on the side of the conveying mechanism 2 and a part extending in the Y direction from this part, and the part extending in the Y direction is provided with long holes 20a extending along the conveying direction Y1.

Figure 6:
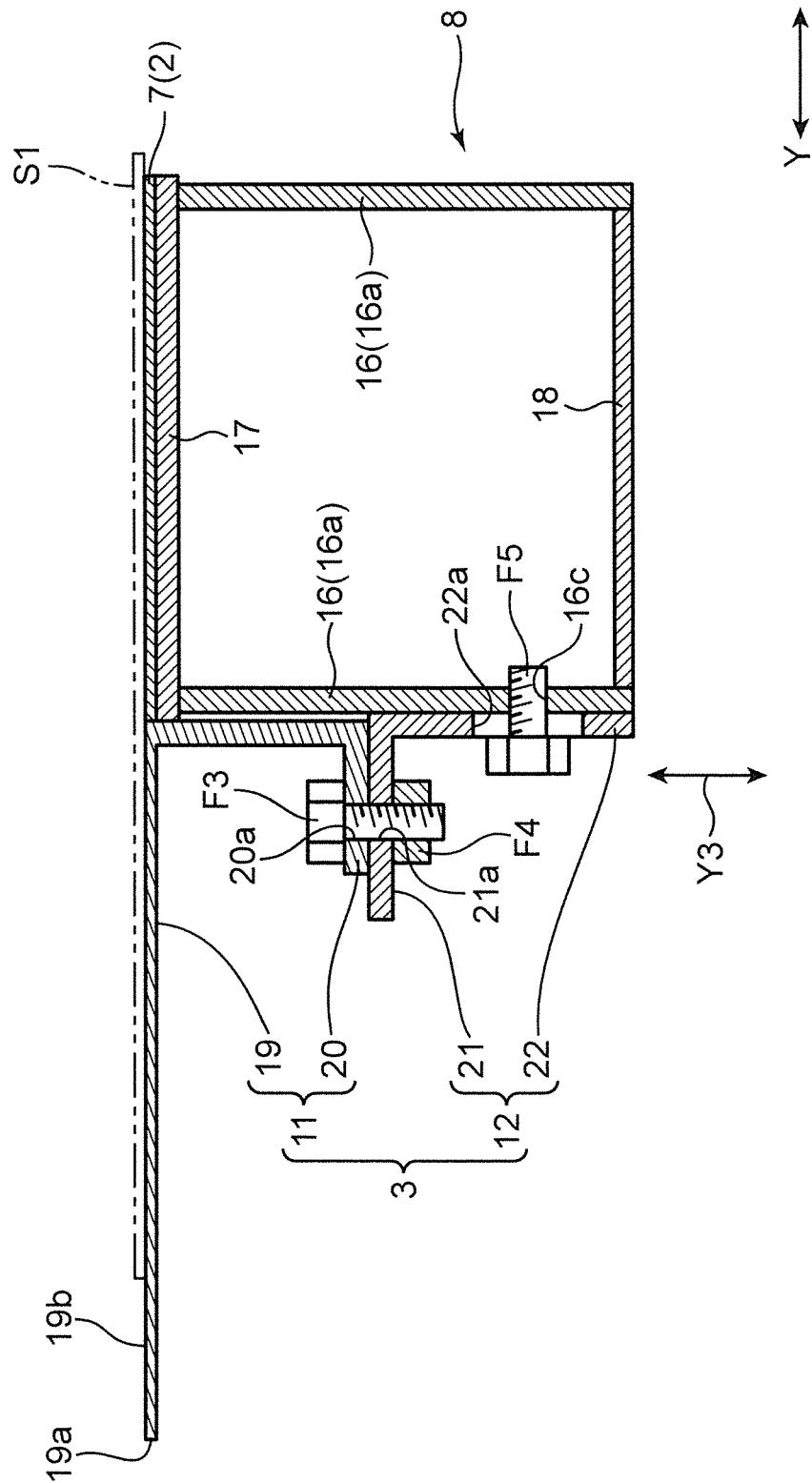
FIG. 6 is a sectional view along line VI-VI of FIG. 4.

As shown in FIG. 6, the bracket 12 includes an attached portion 21 having the attaching portion 20 attached thereon and a fixing portion 22 fixed to the side plate 16 of the pulley supporting portion 8.

The attached portion 21 includes insertion holes 21a provided along the attaching portion 20, and bolts F3 inserted into the long holes 20a are inserted through the insertion holes 21a. Nuts F4 are fastened to bolts F3 inserted through the insertion holes 21a, whereby the second folding member 11 and the bracket 12 are fixed.

The fixing portion 22 is configured to fix the bracket 12 to the side plate 16 such that the bracket 12 is movable relative to the conveying mechanism 2 in a moving direction Y3 (see FIG. 6) orthogonal to the conveying direction Y1 and the Y direction. Specifically, the fixing portion 22 includes a long hole 22a provided along the side plate 16 and extending along the moving direction Y3. The bracket 12 is fixed to the side plate 16 by tightening a bolt F5 inserted into the long hole 22a into an internally threaded portion 16c formed in the side plate 16.

Accordingly, the second folding line forming portion 19a can be moved relative to the conveying mechanism 2 along the moving direction Y2 (see FIG. 4) by loosening the nuts F4 and adjusting the positions of the bolts F3 in the long holes 20a.

Further, the second folding line forming portion 19a can be moved relative to the conveying mechanism 2 along the moving direction Y3 (see FIG. 5) by loosening the bolt F5 and adjusting the position of the bolt F5 in the long hole 22a.

Next, the third folding member 4 is described with reference to FIGS. 1, 3, 5 and 7.

The third folding member 4 is attached to the downstream portion 16b of the side plate 16 distant from the main frame 5a of the pulley supporting portion 8.

The third folding member 4 includes a third folding portion 14 for forming the third and fourth folding lines B3, B4 of the sheet S1 and a fixing portion 15 bent along the side plate 16 from an end part of the third folding portion 14 in the Y direction and fixed to the side plate 16.

The third folding portion 14 includes a fourth folding line forming portion 14b for folding the sheet S1 along the fourth folding line B4 such that one widthwise part of the sheet S1 folded by the second folding portion 19 is parallel to another part and a third folding line forming portion 14a for reversing one widthwise part of the sheet S1 folded along the fourth folding line B4 along the third folding line B3.

The fourth folding line forming portion 14b is an edge part of the third folding portion 14 extending in the X direction along the side plate 16.

The third folding line forming portion 14a is an edge part of the third folding portion 14 inclined from the side plate 16 on the side of the fixing portion 15 out of the both side plates 16 toward the other side plate 16 as it extends toward a downstream side in the conveying direction Y1. That is, the third folding portion 14 is shaped to cover the conveying belt 7 in a wide range as it extends toward the downstream side in the conveying direction Y1.

The fixing portion 15 is configured to fix the third folding portion 14 to the side plate 16 such that the third folding portion 14 is arranged above the conveying belt 7 with a gap G1 (see FIG. 7) defined therebetween. The gap G1 is so dimensioned that the folded sheet S1 is insertable thereinto.

Next, functions of the folding device described above are described.

Figure 4:
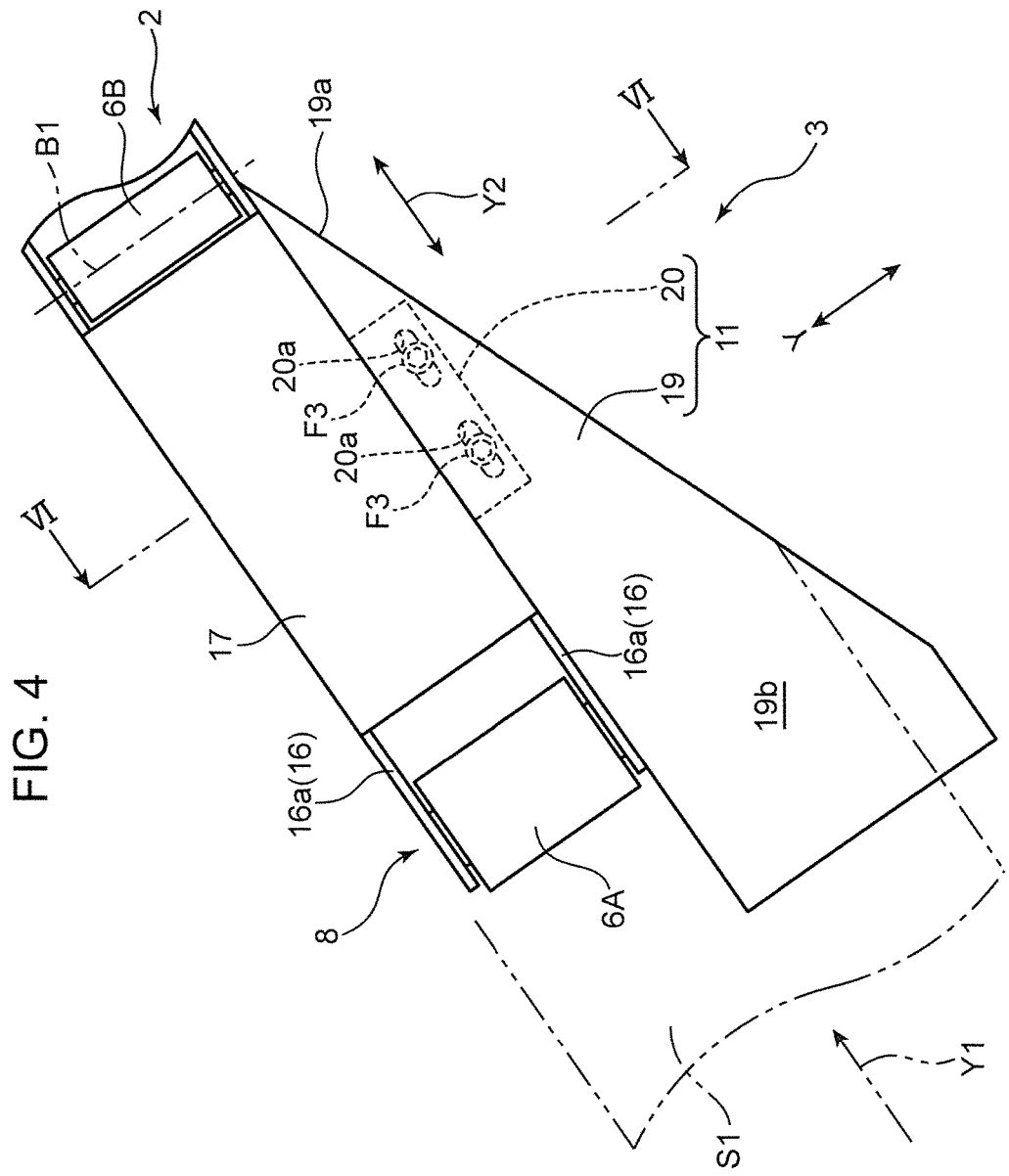
FIG. 4 is a view indicated by an arrow IV of FIG. 3.

As shown in FIG. 4, the sheet S1 being conveyed by the conveying mechanism 2 is conveyed along the longitudinal direction thereof while being bent along the first folding line B1 specified by the second pulley 6B.

One widthwise part P1 (see FIG. 1) of the sheet S1 folded along the first folding line B1 is supported by the conveying belt 7 (not shown) provided between the second and third pulleys 6B, 6C as shown in FIG. 5. Specifically, a part of the sheet S1 is supported in the gap G1 (see FIG. 7) between the conveying belt 7 and the third folding portion 14.

Further, as shown in FIG. 4, the sheet S1 being conveyed by the conveying mechanism 2 is supported by the conveying belt 7 (not shown) provided between the first and second pulleys 6A, 6B and the supporting surface 19b of the second folding portion 19.

Here, since the second folding line forming portion 19a of the second folding portion 19 is inclined toward the side plate 16 as it extends toward the downstream side in the conveying direction Y1, the sheet S1 is gradually folded along the second folding line forming portion 19a as being conveyed.

Figure 8:
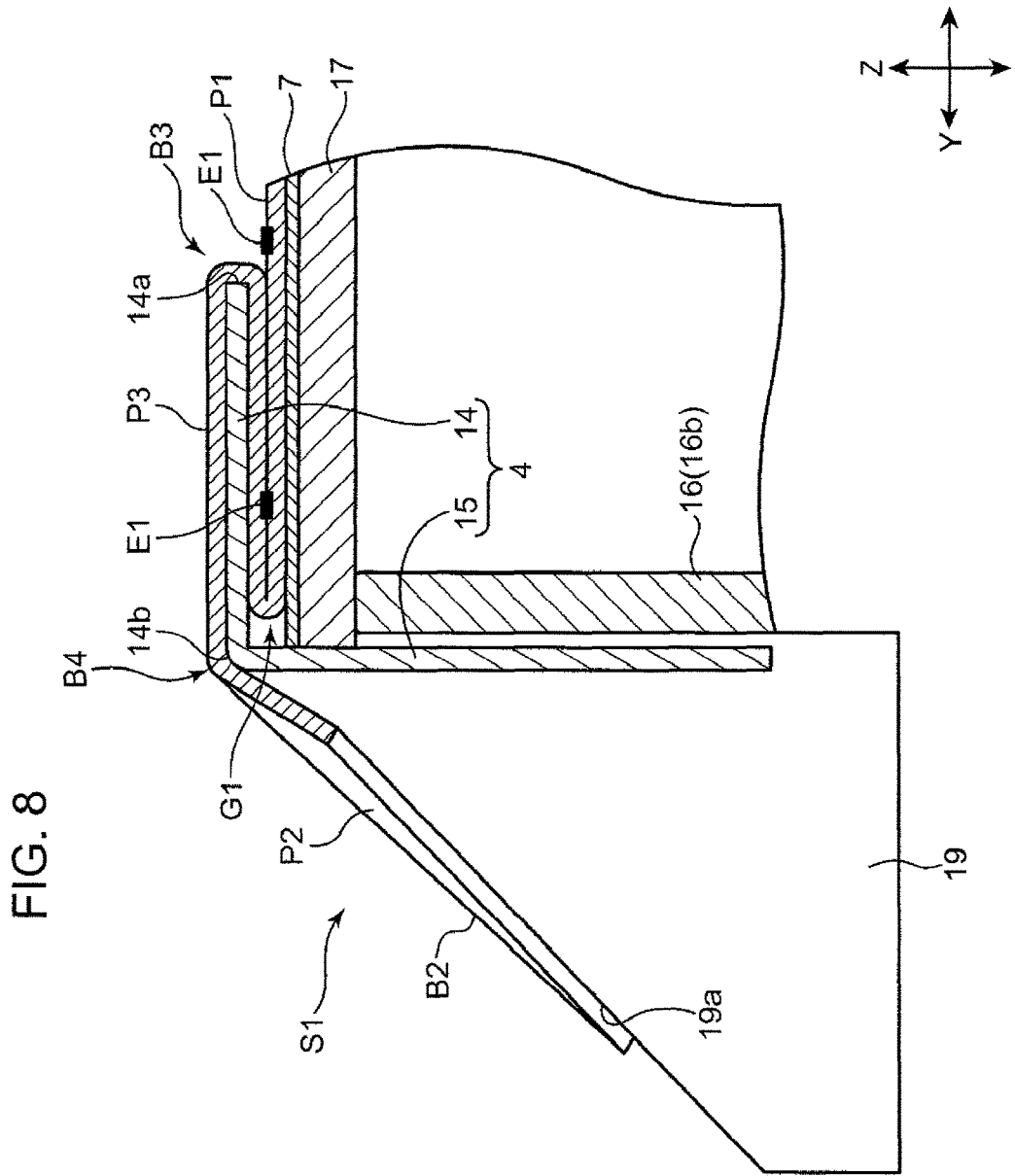
FIG. 8 is a sectional view along line VIII-VIII of FIG. 5.

One widthwise part P2 (see FIG. 1) of the sheet S1 folded along the second folding line forming portion 19a is arranged along a side surface of the conveying mechanism 2 in the Y direction as shown in FIGS. 3 and 8.

The one widthwise part P2 of the sheet S1 is folded along the fourth folding line forming portion 14b to be parallel to the part P1 as shown in FIGS. 5 and 8. One widthwise part P3 (see FIG. 1) of the sheet S1 folded along the fourth folding line forming portion 14b is arranged above the third folding portion 14.

Here, since the third folding line forming portion 14a of the third folding portion 14 is inclined in the Y direction as it extends toward the downstream side in the conveying direction Y1, the part P3 of the sheet S1 is gradually reversed along the third folding line forming portion 14a as being conveyed, and is introduced into the gap G1 (see FIGS. 7 and 8) between the third folding portion 14 and the conveying belt 7.

In this way, the sheet S1 is folded such that one widthwise part thereof overlaps with another part.

Here, in the case of changing a thickness of the sheet S1 or a tension applied to the sheet S1, the attached position of the second folding portion 19 with respect to the conveying mechanism 2 is adjusted, whereby the sheet S1 can be properly folded by adjusting areas of the widthwise parts P2, P3 of the sheet S1 located between the second and third folding lines B2, B3.

A folding method for folding the sheet S1 using the folding device 1 described above is described below.

The folding method includes a conveying step, a folding line forming step and an adjusting step.

In the conveying step, the sheet S1 is conveyed in its longitudinal direction using the conveying mechanism 2.

In the folding line forming step, the first, second, third and fourth folding lines B1, B2, B3 and B4 of the sheet being conveyed by the conveying step are formed using the second folding mechanism 3 and the third folding member 4.

In the adjusting step, a folded state of the sheet S1 is adjusted by moving the second folding line forming portion 19a of the second folding member 11 with respect to the formation positions of the first and third folding lines B1, B3 prior to the folding line forming step.

By performing the adjusting step, the folded state of the sheet S1 can be adjusted prior to the folding line forming step in the case of changing the thickness of the sheet S1 or a tension applied to the sheet S1, wherefore the sheet S1 can be precisely folded.

As described above, the formation position of the second folding line B2 can be changed with respect to those of the first and third folding lines B1, B3 (positions of the second pulley 6B and the third folding member 4) with the formation positions of the first and third folding lines B1, B3 maintained by adjusting the attached position of the second folding member 11 with respect to the conveying mechanism 2.

Since the areas of the widthwise parts P2, P3 of the sheet located between the second and third folding lines B2, B3 can be adjusted in this way, the sheet S1 can be precisely folded even in the case of changing the thickness of the sheet S1 or a tension applied to the sheet S1.

Further, according to the above embodiment, the following effects can be exhibited.

In the above embodiment, the conveying belt 7 is interposed between the second pulley 6B for forming the first folding line B1 and the sheet S1 and the sheet S1 can be conveyed by the movement of this conveying belt 7. Thus, the deterioration of the sheet S2 by friction with the upstream side plate 30 for forming the first folding line B5 as in the prior art shown in FIG. 9 can be prevented.

Here, since the second pulley 6B (conveying belt 7) and the sheet S1 are in contact over a predetermined range in a circumferential direction of the second pulley 6B, the first folding line B1 formed by this second pulley 6B also has a predetermined width in the circumferential direction and it may not be possible to precisely fold the sheet S1 depending on the formation position of the second folding line B2 with respect to that of the first folding line B1.

However, since the formation position of the second folding line B2 with respect to that of the first folding line B1 can be relatively adjusted by adjusting the position of the second folding member 11 as described above, the prevention of the deterioration of the sheet S1 and the precise folding of the sheet S1 can be accomplished.

Further, according to the above embodiment, the sheet S1 can be folded in two stages by being reversed along the third folding line B3 after the one widthwise part of the sheet S1 bent along the second folding line B2 is bent in the width direction along the fourth folding line B4.

Figure 9A:
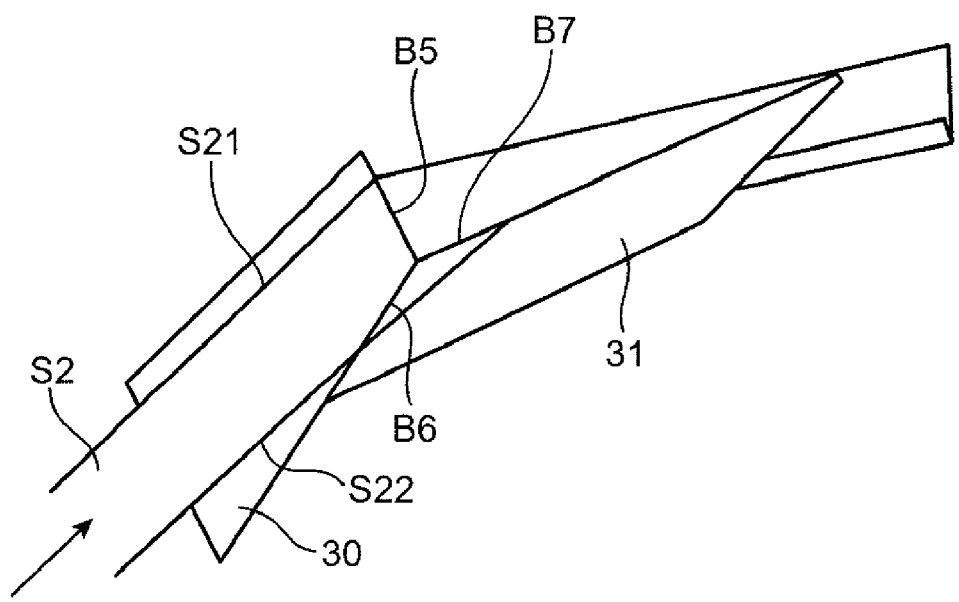
FIG. 9A is a perspective view enlargedly showing an essential part of a conventional device in a state where a sheet is being folded.
Figure 9B:
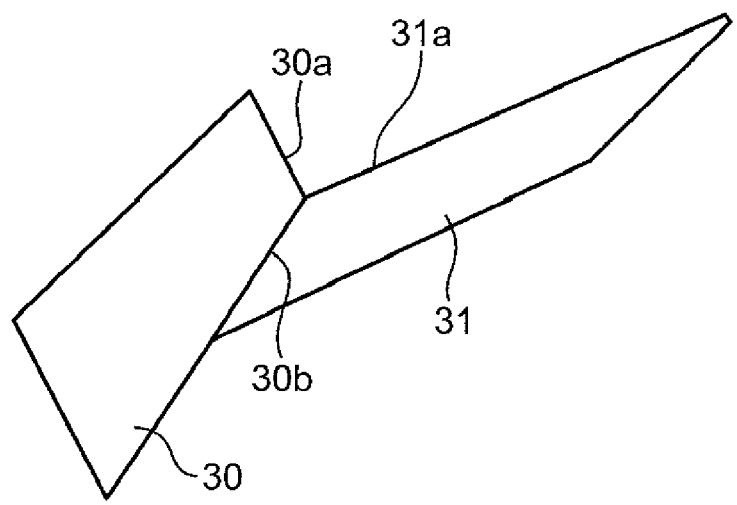
FIG. 9B is a perspective view enlargedly showing the essential part of the conventional device in the state of FIG. 9A with the sheet omitted.

Accordingly, a direction changing angle of the sheet S1 at the third folding line B3 can be made smaller as compared to the case where one widthwise part of the sheet S2 folded along the second folding line B6 is directly folded along the third folding line B7 as in the prior art shown in FIG. 9.

Since a tension produced in the sheet S1 between the second and third folding lines B2, B3 can be reduced in this way, a load of the sheet S1 can be alleviated.

Note that the specific embodiment described above mainly includes inventions having the following configurations.

Specifically, the present invention provides a folding device for folding a sheet in a width direction such that one widthwise part of the sheet overlaps with another part while conveying the sheet in a longitudinal direction thereof, the folding device including a conveying mechanism configured to convey the sheet in the longitudinal direction and a folding mechanism configured to form a first folding line, a second folding line and a third folding line of the sheet being conveyed by the conveying mechanism, the first folding line extending in the width direction from one widthwise end to a widthwise intermediate part of the sheet, the second folding line extending obliquely to the longitudinal direction from the other widthwise end of the sheet on a side upstream of the first folding line in a conveying direction toward an end of the first folding line and the third folding line being configured to reverse one widthwise part of the sheet such that one widthwise part of the sheet folded along the second folding line overlaps with another part on a side downstream of the first folding line in the conveying direction, wherein the folding mechanism includes a second folding member having a second folding line forming portion configured to form the second folding line of the sheet and the second folding member is so attached to the conveying mechanism that the second folding line forming portion is movable with respect to the formation positions of the first and third folding lines of the sheet.

In the present invention, the formation position of the second folding line can be changed with respect to those of the first and third folding lines with the formation positions of the first and third folding lines maintained by adjusting the attached position of the second folding member with respect to the conveying mechanism.

Since an area of one widthwise part of the sheet located between the second and third folding lines can be adjusted in this way, the sheet can be precisely folded even in the case of changing a thickness of the sheet or a tension applied to the sheet.

As before, the first folding line may be formed by sliding the sheet and a plate. However, in this case, the sheet may be deteriorated by friction between the sheet and the plate.

Accordingly, in the above folding device, the conveying mechanism preferably includes a conveying belt and a plurality of pulleys having the conveying belt provided thereon along an annular path including a conveyance path bent at a position corresponding to the first folding line and conveys the sheet along the conveyance path by a movement of the conveying belt, and the folding mechanism preferably includes a pulley provided at the bent position of the conveyance path out of the plurality of pulleys and configured to form the first folding line of the sheet.

In the above mode, the conveying belt is interposed between the pulley for forming the first folding line and the sheet and the sheet can be conveyed by the movement of this conveying belt, wherefore the deterioration of the sheet by friction with a member for forming the folding line as before can be prevented.

Here, since the pulley (conveying belt) and the sheet are in contact over a predetermined range in a circumferential direction of the pulley, the first folding line formed by this pulley also has a predetermined width in the circumferential direction and it may not be possible to precisely fold the sheet depending on the formation position of the second folding line with respect to that of the first folding line.

However, since the formation position of the second folding line with respect to that of the first folding line can be relatively adjusted by adjusting the position of the second folding member as described above, the prevention of the deterioration of the sheet and the precise folding of the sheet can be accomplished.

One widthwise part of the sheet folded along the second folding line may be directly reversed along the third folding line as before. However, in this case, the direction of the sheet needs to be suddenly changed at the third folding line. Thus, a tension produced in the sheet becomes large between the second and third folding lines.

Accordingly, in the folding device, the folding mechanism preferably includes a third folding member having a fourth folding line forming portion configured to form a fourth folding line for folding the sheet such that one widthwise part of the sheet folded along the second folding line at a position downstream of the first folding line in the conveying direction is parallel to another part and a third folding line forming portion configured to form the third folding line on one widthwise part of the sheet folded along the fourth folding line.

According to the above mode, the sheet can be folded in two stages by reversing one widthwise part along the third folding line after bending the one widthwise part of the sheet bent along the second folding line in the width direction along the fourth folding line.

Thus, the tension produced in the sheet between the second and third folding lines can be reduced by making a direction changing angle of the sheet at the third folding line smaller, whereby a load of the sheet can be alleviated.

The second folding member may be, for example, configured to be movable relative to the conveying mechanism along the conveying direction of the sheet and/or a direction orthogonal to the conveying direction.

Further, the present invention provides a folding method for folding a sheet in a width direction such that one widthwise part of the sheet overlaps with another part using the above folding device, the folding method including a conveying step of conveying the sheet in a longitudinal direction thereof using the conveying mechanism, a folding line forming step of forming a first folding line, a second folding line and a third folding line of the sheet being conveyed by the conveying step using the folding mechanism, the first folding line extending in the width direction from one widthwise end to a widthwise intermediate part of the sheet, the second folding line extending obliquely to the longitudinal direction from the other widthwise end of the sheet on a side upstream of the first folding line in a conveying direction toward an end of the first folding line and the third folding line being configured to reverse one widthwise part of the sheet such that one widthwise part of the sheet folded along the second folding line overlaps with another part on a side downstream of the first folding line in the conveying direction, and an adjusting step of adjusting a folded state of the sheet by moving the second folding line forming portion of the second folding member with respect to the formation positions of the first and third folding lines prior to the folding line forming step.

According to the present invention, the sheet can be precisely folded in the case of changing a thickness of the sheet or a tension applied to the sheet since the folded state of the sheet can be adjusted prior to the folding line forming step.

The invention claimed is:

1. A folding device for folding a sheet in a width direction such that one widthwise part of the sheet overlaps with another part of the sheet while conveying the sheet in a longitudinal direction thereof, comprising:
   a conveying mechanism configured to convey the sheet in the longitudinal direction; and
   a folding mechanism configured to form a first folding line, a second folding line and a third folding line of the sheet being conveyed by the conveying mechanism, the first folding line extending in the width direction from one widthwise end to a widthwise intermediate part of the sheet, the second folding line extending obliquely to the longitudinal direction from the other widthwise end of the sheet on a side upstream of the first folding line in a conveying direction toward an end of the first folding line and the third folding line being configured to reverse one widthwise part of the sheet such that one widthwise part of the sheet folded along the second folding line overlaps with another part on a side downstream of the first folding line in the conveying direction,
   wherein:
   the folding mechanism includes a second folding line folding member having a second folding line forming portion configured to form the second folding line of the sheet; and the second folding line folding member is attached to the conveying mechanism such that the second folding line forming portion is movable with respect to folding members configured to fold the first and third folding lines of the sheet.

2. The folding device of claim 1, wherein:

the conveying mechanism includes a conveying belt and a plurality of pulleys having the conveying belt provided thereon along an annular path including a conveyance path bent at a position corresponding to the first folding line and conveys the sheet along the conveyance path by a movement of the conveying belt; and the folding mechanism includes a pulley provided at a bent position of the conveyance path out of the plurality of pulleys and configured to form the first folding line of the sheet.

3. The folding device of claim 1, wherein the folding mechanism includes a third folding line folding member having a fourth folding line forming portion configured to form a fourth folding line for folding the sheet such that one widthwise part of the sheet folded along the second folding line at a position downstream of the first folding line in the conveying direction is parallel to another part and a third folding line forming portion configured to form the third folding line on one widthwise part of the sheet folded along the fourth folding line.

4. The folding device of claim 1, wherein the second folding line folding member is attached to the conveying mechanism so as to be movable relative to the conveying mechanism along the conveying direction of the sheet.

5. The folding device of claim 1, wherein the second folding line folding member is attached to the conveying mechanism so to be movable relative to the conveying mechanism along a direction orthogonal to the conveying direction of the sheet.

6. The folding device of claim 1, wherein the folding mechanism includes a first folding line folding member configured to form the first folding line of the sheet, and a third folding line folding member configured to form the third folding line, the folding device further comprising a support for supporting the first folding line folding member, the second folding line folding member and the third folding line folding member, wherein the first folding line folding member and the third folding line folding member are attached to the support, and the second folding line folding member is attached to the support so as to be movable relative to the support.

7. The folding device of claim 6, wherein the first folding line folding member and the third folding line folding member are fixed to the support.

8. A folding method for folding a sheet in a width direction such that one widthwise part of the sheet overlaps with another part using the folding device of claim 1, the method comprising:

a conveying step of conveying the sheet in a longitudinal direction thereof using the conveying mechanism;

a folding line forming step of forming a first folding line, a second folding line and a third folding line of the sheet being conveyed by the conveying step using the folding mechanism, the first folding line extending in the width direction from one widthwise end to a widthwise intermediate part of the sheet, the second folding line extending obliquely to the longitudinal direction from the other widthwise end of the sheet on a side upstream of the first folding line in a conveying direction toward an end of the first folding line and the third folding line being configured to reverse one widthwise part of the sheet such that one widthwise part of the sheet folded along the second folding line overlaps with another part on a side downstream of the first folding line in the conveying direction; and an adjusting step of adjusting a folded state of the sheet by moving the second folding line forming portion of the second folding line folding member with respect to folding members configured to fold the first and third folding lines prior to the folding line forming step.

* * * * *